(12) United States Patent
Chang et al.

(10) Patent No.: US 6,346,418 B1
(45) Date of Patent: Feb. 12, 2002

(54) METHOD FOR EVALUATION OF METAL IMPURITY IN LITHOGRAPHIC MATERIALS

(75) Inventors: Hui-An Chang, Taipei; Bor-Jen Cheng, Hsin-Chu; Yu-Chuan Lin, Chu-Pei, all of (TW)

(73) Assignee: Mosel Vitelic Inc. (TW)

( * ) Notice: Subject to any disclaimer, the term of this patent is extended or adjusted under 35 U.S.C. 154(b) by 0 days.

(21) Appl. No.: 09/388,929

(22) Filed: Sep. 2, 1999

(30) Foreign Application Priority Data

Jun. 25, 1999 (TW) .................................. 88110707 A

(51) Int. Cl.$^7$ .............................................. G01N 33/20
(52) U.S. Cl. ............................ 436/79; 436/73; 436/77; 436/80; 436/81; 436/82; 436/83; 436/84; 436/85; 436/155; 436/173; 436/174; 436/175; 436/182
(58) Field of Search ........................ 436/73, 77, 79–85, 436/155, 171, 172, 173, 174, 175, 182

(56) References Cited

U.S. PATENT DOCUMENTS 5,945,342 A * 8/1999 Maxwell, III et al. ......... 436/81

OTHER PUBLICATIONS

V. Carbonell et al, Anal. Chim. Acta 1990, 238, 417–421.*
E. A. Fitzgerald et al, J. Electrochem. Soc. 1992, 139, 1413–1414.*
T. Y. Chang et al, Chem. Abstr. 1992, 116, abstract 206964q.*
M. Takenaka et al, Chem. Abstr. 1993, 119, abstract 39810q.*
C. Y. Zhou et al, Anal. Chim. Acta 1995, 314, 121–130.*
H. Lippo et al, Chem. Abstr. 1995, 123, abstract 222105k.*
M. Takenaka et al, Analyst 1997, 122, 129–132.*
J. Wang et al, Chem. Abstr. 1997, 127, abstract 88829b.*
C.–C. Huang et al, Anal. Chem. 1997, 69, 3930–3939.*
D. Gh. Ulieru SPIE 1998, 3332, 721–726.*
K. D. Besecker et al, Chem. Abstr. 1998, 129, abstract 5195j.*
T. C. O. Da Fonseca et al, Chem. Abstr. 1998, 129, abstract 97435p.*

* cited by examiner

Primary Examiner—Arlen Soderquist

(57) ABSTRACT

A method for evaluating ratios of metallic impurities in lithographic materials is disclosed. The method comprises: separating said metal from said lithographic material by microwave heating; then adding said metal to an acid to form a solution; and finally analyzing said solution by a instrument to measure ratio of said metal.

6 Claims, 2 Drawing Sheets

METHOD FOR EVALUATION OF METAL IMPURITY IN LITHOGRAPHIC MATERIALS

BACKGROUND OF THE INVENTION

1. Field of the Invention

The present invention relates a method for evaluation of metallic impurities in lithographic materials, more particularly to a method for evaluation of metallic impurities in lithographic materials.

2. Description of the Prior Art

As device dimensions are scaled down in ULSI circuits, the purity of process chemicals is becoming a major concern. It is inevitable for the section of incoming quality (IQC) or quality reliability assurance (QRA) to regulate a strict standard method to ensure the reliability of process chemicals. Due to stringent requirements for detection limit and precision in trace metal in the semiconductor industry, the choice of analytical technology poses a challenging problem.

The lithographic materials applied repeatedly onto a wafer surface play a very important role in the semiconductor process. It is interesting to find out trace metallic impurities in lithographic materials. Based on the complex organic matrix in lithographic materials such as BRAC, i-line resist and DUV resist. It is not easy to determine multi-element directly by an instrument. In this work, the lithographic materials are first decomposed by a closed-vessel microwave oven for the determination of metallic impurities of multi-element by ICP-MS.

The conventional method to evaluate metallic impurities in incoming lithographic materials is shown in FIG. 1. A sample is digested with acids on a hot plate to remove the polymer matrix (e.g. C. H. compounds) in this sample. The digested sample is measured by a graphite furnace atomic absorption spectrometer (GFAAS). The problems of this conventional method are described as follows:

(1) The heating efficiency of a hot plate is not good enough for digesting lithographic materials. It could not remove the polymer matrixes of samples thoroughly. The more matrixes left in a sample the more complicated to measure the metallic impurities.

(2) When samples are digested on a hot plate that is in an opened environment the samples are easily contaminated during the digestion thus the analyzed data will be varied.

(3) The throughput of GFAAS is not fast enough which compares with ICP-MS. Only one element could be measured at a time by GFAAS. It takes 1.5 to 2 hours to measure one sample for measuring eight elements by GFAAS.

For the foregoing reasons, it is necessary to develop a new method to improve the efficiency of digestion and measurement to get more precise results.

SUMMARY OF THE INVENTION

According to the present invention, a new method is provided for evaluating ratios of metallic impurities in a photoresist that substantially increases the digesting efficiency and throughput. In one embodiment, the photoresist and nitric acid are put into a closed-vessel tube. The mixture in the tube containing both the photoresist and nitric acid is heated by microwave to do the first digestion. Subsequently, hydrogen peroxide is added into the mixed liquid in the former tube and then is heated in order to do the second digestion. The left liquid mixture is pre-concentrated by a hot plate and then to rinse with 1% nitric acid. The solution of 1% nitric acid with the photoresist residues after digestion is measured by ICP-MS to get the concentration of metallic impurities in the sample.

BRIEF DESCRIPTION OF THE DRAWINGS

The foregoing paragraphs and many of the obvious advantages of this invention will become more readily appreciated and better understood by the following detailed description, which can be taken in conjunction with the accompanying drawings, wherein.

DESCRIPTION OF THE PREFERRED EMBODIMENT

Figure 1:
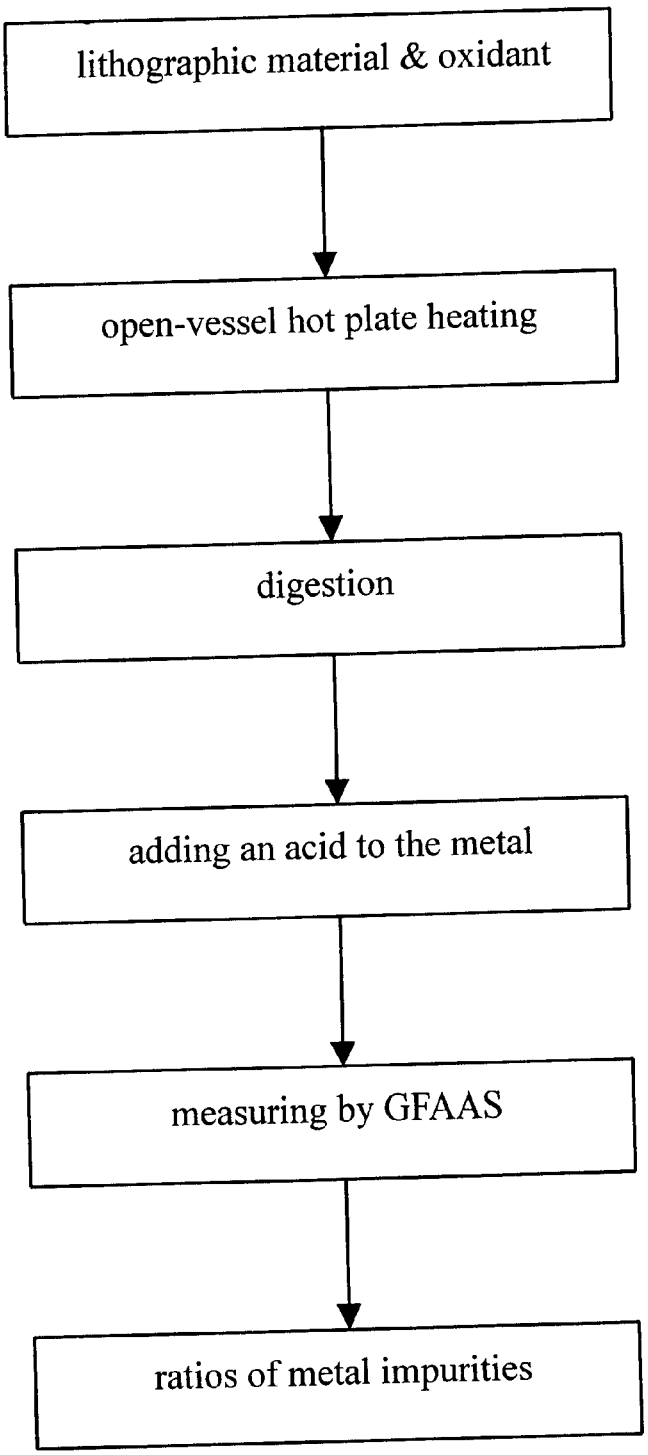
FIG. 1 shows the conventional procedures.
Figure 2:
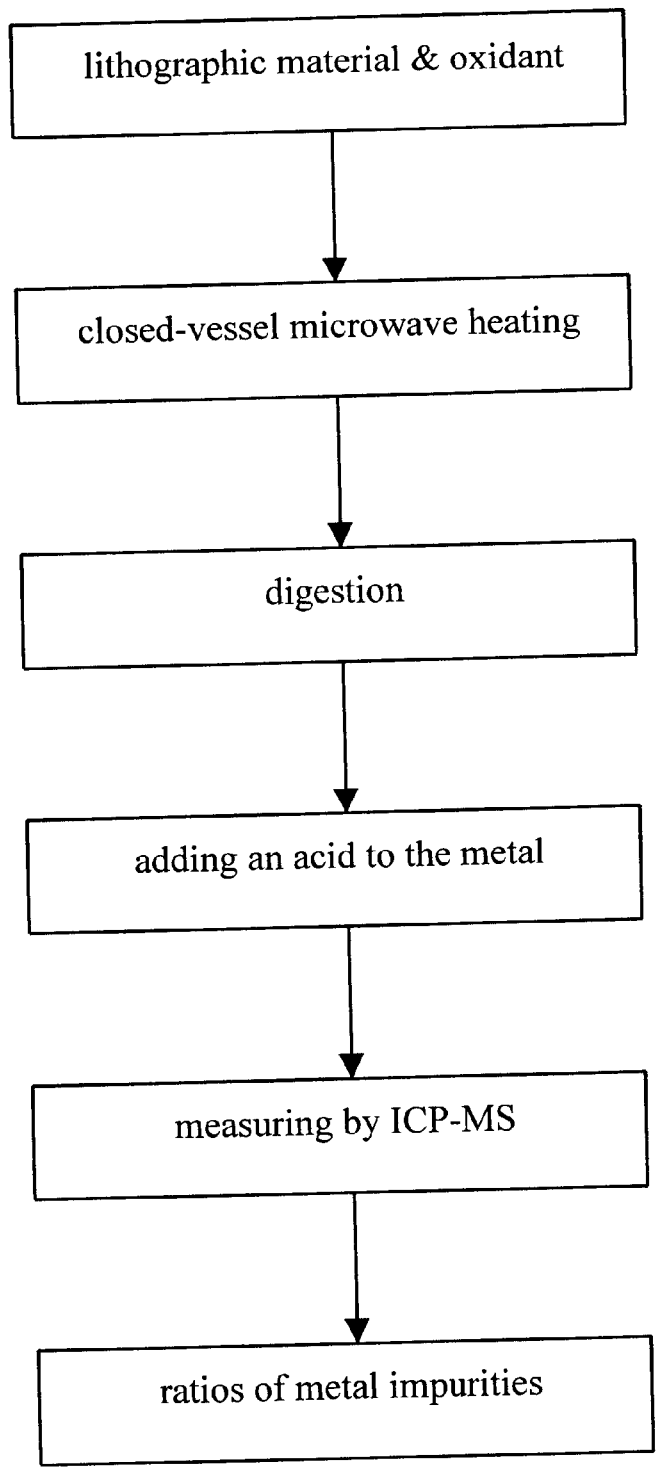
FIG. 2 shows the procedures disclosed by the present invention.

The procedures for the present invention are shown in FIG. 2 and the Model MDS-2000 (CEM, Matthews, N.C.) closed-vessel microwave oven is used. In one embodiment, 0.25 mL of lithographic material, such as photoresist, is put into the closed-vessel microwave oven equipped with a teflon-coated cavity and a removable 12-position sample carousel. The oven has a variable power range (up to 630W) adjustable in 1% increments. The existing turntable is rotated at 3.5 rev/min and a pressure line was installed with a transducer for pressure monitoring. The pressure limit was set at 150 psi, a gas pressure in the vessel over the setting pressure limit could result in the heating power turned off; however, when the pressure dropped to 148 psi, the power was restarted to heat the samples. The sample was digested in a lined digestion vessel (100 mL volume, maximum operating pressure 200 psi) consisting of a chemically resistant inner liner (Teflon PFA) and cover to contain and isolate the sample solution from a higher strength outer pressure vessel body. In order to protect the digestion vessel from excessive pressures, a rupture membrane was used to direct the escape gases through the exhaust port if the safety rupture membrane broke.

The digested reaction has two steps and the lithographic materials also include bottom anti-reflective coating (BARC) and top anti-reflective coating (TARC). The photoresist (PR) mentioned above includes KrF PR, DUV PR, i-line PR, and g-line PR, all that contain organic polymers and metallic impurities such as Cr, Fe, Ni, Cu, Zn ,Au, Pb, S n, Pt, C s, Na, Ca, and Al.

In the first step of the reaction, the 1.5 mL 70% nitric acid is added, the power is applied to 40% W, and the reaction time is 30 minutes. The 70% nitric acid is a strong oxidant which can decompose most of the polymers in the photoresist into carbon dioxide ($CO_2$) and water ($H_2O$) that is referred to as digestion. Therefore, the $CO_2$ and $H_2O$ will keep in the reaction tube. The gas phase $CO_2$ and $H_2O$ increase the pressure of reaction tube so as to enhance the completeness of decomposition of polymer matrix.

In the second step of the reaction, the 0.5 mL hydrogen peroxide is added, the power is applied to 55% W, and the reaction time is also 30 minutes. For the step, the hydrogen peroxide plays the same role as the nitric acid mentioned above. After this step, the polymers in the photoresist are almost decomposed. The residual sample is cooled down and transferred into a teflon beaker. The sample solution after digestion was heated with the IR lamp in a clean hood to evaporate to incipient dryness, and subsequently adding with 5 mL 1% nitric acid to rinse the beaker. The final solution can be analyzed the metal impurities by inductively coupled plasma mass spectrometer (ICP-MS) and GFAAS.

In the embodiment, the KrF photoresist (PR) is illustrated in order to digest the KrF PR, two oxidants are used for two steps of reaction respectively because the strategy can provided the highest efficiency than others. For example, it can also complete the work to use just one oxidant such as nitric acid for one step but the organic matrix will be less decomposed.

For the digestion, the present invention heats the photoresist by a closed-vessel microwave oven instead of prior hot plate. For the evaluation of metallic impurities, the ICP-MS can measure more elements than GFAAS in one time.

Although specific embodiments have been illustrated and described, it will be obvious to those skilled in the art that various modifications may be made without departing from what is intended to be limited solely by the appended claims.

What is claimed is:

1. A method for evaluating a ratio of metal in photoresist material, comprising:

putting said photoresist into a reaction tube and adding a first nitric acid solution into said reaction tube to form a first mixed liquid, wherein said photoresist comprises a metal;

heating said first mixed liquid in a microwave oven for digesting a non-metal portion of said photoresist;

monitoring a pressure of said reaction tube during the heating of the first mixed liquid;

adding hydrogen peroxide into said reaction tube to form a second mixed liquid and heating said second mixed liquid to continue digesting the photoresist;

monitoring a pressure of said reaction tube during the heating of the second mixed liquid;

evaporating residual liquid left after heating of said second mixed liquid by hot plate heating to form a residue containing said metal;

forming a solution by adding a second nitric acid solution to said residue; and analyzing said solution by ICP-MS to measure the ratio of said metal.

2. The method according to claim 1, wherein said metal is selected from the group consisting of Cr, Fe, Ni, Cu, Zn, Au, Pb, Sn, Pt, Cs, Na, Ca, and Al.

3. The method according to claim 1, wherein said photoresist is selected from the group consisting of KrF PR, i-line PR, g-line PR, and DUV PR.

4. The method according to claim 1, wherein said first nitric acid solution is 70% nitric acid.

5. The method according to claim 1, wherein said second nitric acid solution is 1% nitric acid.

6. The method according to claim 1, wherein said microwave oven is a closed-vessel microwave oven.

* * * * *